(12) United States Patent
Xu et al.

(10) Patent No.: US 12,239,323 B2
(45) Date of Patent: Mar. 4, 2025

(54) LEFT ATRIAL APPENDAGE LIGATOR

(71) Applicant: NANJING DRUM TOWER HOSPITAL, Jiangsu (CN)

(72) Inventors: Can Xu, Jiangsu (CN); Dongjin Wang, Jiangsu (CN)

(73) Assignee: NANJING DRUM TOWER HOSPITAL, Nanjing (CN)

( * ) Notice: Subject to any disclaimer, the term of this patent is extended or adjusted under 35 U.S.C. 154(b) by 0 days.

(21) Appl. No.: 18/708,999

(22) PCT Filed: Aug. 16, 2023

(86) PCT No.: PCT/CN2023/113352
§ 371 (c)(1),
(2) Date: May 9, 2024

(87) PCT Pub. No.: WO2024/051460
PCT Pub. Date: Mar. 14, 2024

(65) Prior Publication Data
US 2024/0325025 A1    Oct. 3, 2024

(30) Foreign Application Priority Data
Sep. 6, 2022 (CN) .......................... 202211086543.0

(51) Int. Cl.
*A61B 17/12* (2006.01)

(52) U.S. Cl.
CPC .. *A61B 17/12122* (2013.01); *A61B 17/12031* (2013.01); *A61B 17/1214* (2013.01); *A61B 2017/12054* (2013.01)

(58) Field of Classification Search
CPC ........ A61B 17/12122; A61B 17/12031; A61B 17/1214; A61B 17/12; A61B 17/12009;
(Continued)

(56) References Cited

U.S. PATENT DOCUMENTS

| 2009/0204125 A1 | 8/2009 | Onishi et al. |
| 2013/0267965 A1 | 10/2013 | Miziguchi et al. |
| 2015/0190135 A1 | 7/2015 | Ibrahim et al. |

FOREIGN PATENT DOCUMENTS

| CN | 101057789 A | 10/2007 |
| CN | 102448383 A | 5/2012 |

(Continued)

*Primary Examiner* — Katherine M Shi
*Assistant Examiner* — Mohammed S Adam
(74) *Attorney, Agent, or Firm* — MUNCY, GEISSLER, OLDS & LOWE, P.C.

(57) ABSTRACT

A left atrial appendage ligator having a ligature and operating handle. One end of the operating handle is fixedly connected with a support rod, the inner wall of the support rod is fixedly connected with a feeding pipe and locking pipe. A first sliding groove is formed in the inner side wall of the feeding pipe. The inner side wall of the first sliding groove is slidably connected with a first sliding block. The middle part of the first sliding block is fixedly connected with a feeding push rod. One end of the feeding push rod is fixedly connected with a first hook. One side of the first sliding block is fixedly connected with a return spring. The left atrial appendage ligator has a locking push rod, ligature, hanger knot and supporting component. The ligature is prearranged on a sleeve pipe portion to form the hanger knot to avoid knotting during the operation process. During operation, the knotting can be completed only by locking the hanger knot. The sleeve pipe portion serves as support for threading the other end of the ligature to avoid automatic locking. After the sleeve pipe portion is separated from the hanger knot, the hanger knot can be pulled for automatic locking.

5 Claims, 5 Drawing Sheets (58) Field of Classification Search
CPC .............. A61B 17/128; A61B 17/1285; A61B 2017/12054; A61B 2017/0023; A61B 2017/00358
See application file for complete search history.

(56) References Cited

FOREIGN PATENT DOCUMENTS

| | | | |
|---|---|---|---|
| CN | 105997180 | A | 10/2016 |
| CN | 106236178 | A | 12/2016 |
| CN | 208808584 | U | 5/2019 |
| CN | 112315519 | A | 2/2021 |
| CN | 112353449 | A | 2/2021 |
| CN | 112716557 | A | 4/2021 |
| CN | 214073411 | U | 8/2021 |

FIG. 5

LEFT ATRIAL APPENDAGE LIGATOR

TECHNICAL FIELD

The present invention relates to the technical field of medical devices and particularly discloses a left atrial appendage ligator.

BACKGROUND

The left atrial appendage (LAA) is a long and narrow tubular blind cavity with irregular shape, has a plurality of sections of tortuosity, has the size equivalent to that of the thumb, and has an opening with the size of 10 mm-40 mm. The LAA abundant pectinate muscles and musculo trabecula, such that the blood flow therein is easy to generate vortex and has a slow speed. Therefore, thrombus is easily formed in the LAA.

Patients with atrial fibrillation (AF) have a significantly increased risk of stroke. Research suggests that cardiogenic thrombus of 60% of patients with rheumatic heart disease combined with AF is from the LAA and 91% of patients with non-valvular AF have stroke caused by the thrombus in the LAA. Therefore, removing the LAA will help reduce left atrial thrombosis and stroke events.

Simultaneously removing or sealing the LAA during cardiac surgery is simple and easy. Therefore, many physicians propose that for such patients, the LAA needs to be removed or sealed simultaneously with the cardiac surgery. However, the surgical trauma is large for removing or sealing of the LAA alone and the surgery is not suitable. Therefore, ligation becomes a preferred treatment mode. However, a traditional ligator is inconvenient to realize automatic knotting, and an external appliance needs to be applied for operation, such that the operation time is long, and the operation quality and efficiency are influenced. Thus, an LAA ligator is provided.

SUMMARY

In order to solve the problem that in the prior art, a traditional ligator is inconvenient to realize automatic knotting, and an external appliance needs to be applied for operation, such that the operation time is long, and the operation quality and efficiency are influenced, the present invention provides a left atrial appendage ligator using the following technical solution:

A left atrial appendage ligator comprises a ligature and an operating handle, one end of the operating handle is fixedly connected with a support rod, the inner wall of the support rod is fixedly connected with a feeding pipe and a locking pipe, a first sliding groove is formed in the inner side wall of the feeding pipe, the inner side wall of the first sliding groove is slidably connected with a first sliding block, the middle part of the first sliding block is fixedly connected with a feeding push rod, one end of the feeding push rod is fixedly connected with a first hook, one side of the first sliding block is fixedly connected with a return spring, a second sliding groove is formed in the inner side wall of the locking pipe, the second sliding groove is internally slidably connected with a second sliding block, one end of the second sliding block is fixedly connected with a second hook, the other end of the second sliding block is fixedly connected with a locking push rod, a sliding cavity is formed in the inner wall, adjacent to the second sliding groove, of the locking pipe, a supporting component is inserted in the sliding cavity, one end of the ligature is wound at the middle part of the ligature to form a hanger knot so as to form a loop at the middle part of the ligature in a surrounding manner, and the loop is arranged at one end of the outer wall of the supporting component.

In the technical solution, the feeding pipe and the locking pipe are both arranged in a detachable structure so as to facilitate an operator to detach the feeding pipe and the locking pipe to change different ligatures, thereby realizing repeated use of the ligator.

Optionally, the feeding pipe comprises a straight pipe portion and a guide portion, and one end of the guide portion is in threaded connection with the straight pipe portion so as to facilitate the operator to detach the feeding pipe and fix the ligature. The locking pipe comprises a fixing portion and a detaching portion, and one end of the detaching portion is in threaded connection with the fixing portion so as to facilitate detaching of the locking pipe and fix the other end of the ligature.

Optionally, one end of the ligature threading through the guide portion is attached to the surface of the first hook, and the other end of the ligature threading through the detaching portion is attached to the surface of the second hook so as to facilitate change of different ligatures during use each time.

Optionally, the supporting component comprises a supporting rod inserted in the movable cavity, one end of the supporting rod is fixedly connected with a sleeve pipe portion, a guide hole for threading the ligature is formed in the middle part of the sleeve pipe portion, and a temporary storage groove matched with the ligature is formed in the outer wall of the sleeve pipe portion. The temporary storage groove can improve the friction force and avoid automatic falling and locking of the ligature.

Optionally, the operating handle comprises a fixed handle, the inner side wall of the fixed handle is rotatably connected with a grip through a rotating shaft, the top part of the grip is provided with a push plate matched with the feeding push rod, and the other end of the feeding push rod pushes tightly against the side wall of the push plate so as to facilitate pushing of the feeding push rod by the push plate to adjust the size of the loop formed by the ligature.

Optionally, the other end of the support rod and one end of the locking push rod are each fixedly connected with a push button, a horizontal sliding groove matched with the push buttons is formed in the upper surface of the fixed handle, and the push buttons are in slip connection with the inner wall of the horizontal sliding groove so as to facilitate controlling of the locking of the ligature and the separation of the sleeve pipe portion from the ligature through the push buttons.

Optionally, the top part of the inner wall of the fixed handle is fixedly connected with a buffer spring, and one end of the buffer spring is fixedly connected with one of the push buttons. Therefore, after the locking, the buffer spring pushes the push button and then discharge the hanger knot, thereby facilitating the operator to cut the ligature.

A method of using the left atrial appendage ligator comprises the following specific steps:

step 1, prearranging the ligature on the sleeve pipe portion to form the hanger knot;

step 2, pressing the grip by an operator, extending the ligature out in a surrounding manner to form a ligature ring, and expanding the ligature ring to pass through the outer contour of the left atrial appendage, wherein the size of the ligature ring is set to be 50-70 mm;

step 3, lowering the ligature ring to pass through the outer contour of the left atrial appendage with the aid of a surgical instrument by the operator to a ligation position;

step 4, confirming that when the ligature ring sleeves the ligation position, sliding backwards the push button at the other end of the support rod by the operator to drive the recovery of the sleeve pipe portion so as to separate the ligature from the sleeve pipe portion, and simultaneously sliding backwards the push button at one end of the locking push rod to drive the locking of the hanger knot so as to realize automatic knotting; and step 5, cutting off the ligature at the tail part of the hanger knot and taking out the left atrial appendage ligator.

Through the technical solution, the operator presses the handle to compress the grip, pushes the feeding push rod through the grip to further push the first sliding block to compress the return spring, such that the feeding push rod extends to drive a movable end of the ligature to extend out and the ligature slides in the sleeve pipe portion when extending out. The hanger knot is supported by the sleeve pipe portion so as to effectively avoid the automatic locking of the hanger knot. Besides, the temporary storage groove is formed in the surface of the sleeve pipe portion, thereby improving the friction force of the surface of the sleeve pipe portion and improving the storage capacity of the ligature. After the ligature ring surrounded by the ligature is expanded, the left atrial appendage can be conveniently and quickly sleeved by the operator. Besides, the ligature is automatically contracted by the return spring. When the hanger knot needs to be locked, the push button at the other end of the support rod slides backward to drive the recovery of the sleeve pipe portion so as to separate the ligature from the sleeve pipe portion, and simultaneously the push button at one end of the locking push rod slides backwards to drive the locking of the hanger knot so as to realize automatic knotting. The ligature is prearranged on the sleeve pipe portion to form the hanger knot so as to avoid knotting during the operation process. During the operation, the knotting can be completed only by locking the hanger knot, thereby reducing the operation time and improving the operation efficiency.

Optionally, a specific operation method for replacing the ligature is further comprised:

detaching the guide portion and the straight pipe portion in a threaded mode by the operator, detaching the detaching portion and the fixing portion in a threaded mode, winding, knotting and fixing the ligature with the first hook, winding the middle part of the ligature to form the hanger knot and hanging same on the sleeve pipe portion, threading the other end of the ligature through the hanger knot, and knotting and fixing same with the second hook.

In the technical solution, the ligature can be conveniently and rapidly replaced, the left atrial appendage ligator can be used for multiple times, and the waste of the instrument is avoided.

The present invention provides the left atrial appendage ligator which has the following beneficial effects:

1. The left atrial appendage ligator is provided with the feeding pipe and the locking pipe in a detachable structure so as to facilitate the operator to detach the feeding pipe and the locking pipe to change different ligatures, thereby realizing repeated use of the ligator.

2. The left atrial appendage ligator is provided with the operating handle, the first sliding block, the first sliding groove, the feeding push rod and the return spring. The first sliding block is in elastic fit to the feeding pipe through the return spring so as to facilitate compression of the return spring by the operating handle to feed the ligature. The ligature ring surrounded by the ligature is expanded so as to facilitate automatic sleeving of the left atrial appendage by the ligature. Besides, the ligature is automatically contracted by the return spring to offer convenience for knotting.

3. The left atrial appendage ligator is provided with the locking push rod, the ligature, the hanger knot and the supporting component. The ligature is prearranged on the sleeve pipe portion to form the hanger knot so as to avoid knotting during the operation process. During the operation, the knotting can be completed only by locking the hanger knot. The sleeve pipe portion serves as a support for threading the other end of the ligature to avoid automatic locking. After the sleeve pipe portion is separated from the hanger knot, the hanger knot can be pulled for automatic locking, thereby reducing the operation time and improving the operation efficiency.

In the figures: 1. ligature; 101. hanger knot; 2. operating handle; 201. fixed handle; 202. grip; 3. feeding pipe; 301. straight pipe portion; 302. guide portion; 4. locking pipe; 401. fixing portion; 402. detaching portion; 5. first sliding groove; 6. first sliding block; 7. first hook; 8. feeding push rod; 9. return spring; 10. second sliding block; 11. second hook; 12. locking push rod; 13. supporting rod; 14. sleeve pipe portion; 15. guide hole; 16. push button; and 17. buffer spring.

DETAILED DESCRIPTION

The technical solutions in the examples of the present invention will be clearly and completely described below with reference to the drawings in the examples of the present invention. It is obvious that the described examples are only a part of the examples of the present invention, and not all of the examples. All other examples obtained by a person of ordinary skill in the art based on the examples of the present invention without creative efforts shall fall within the protection scope of the present invention.

Example 1

Figure 1:
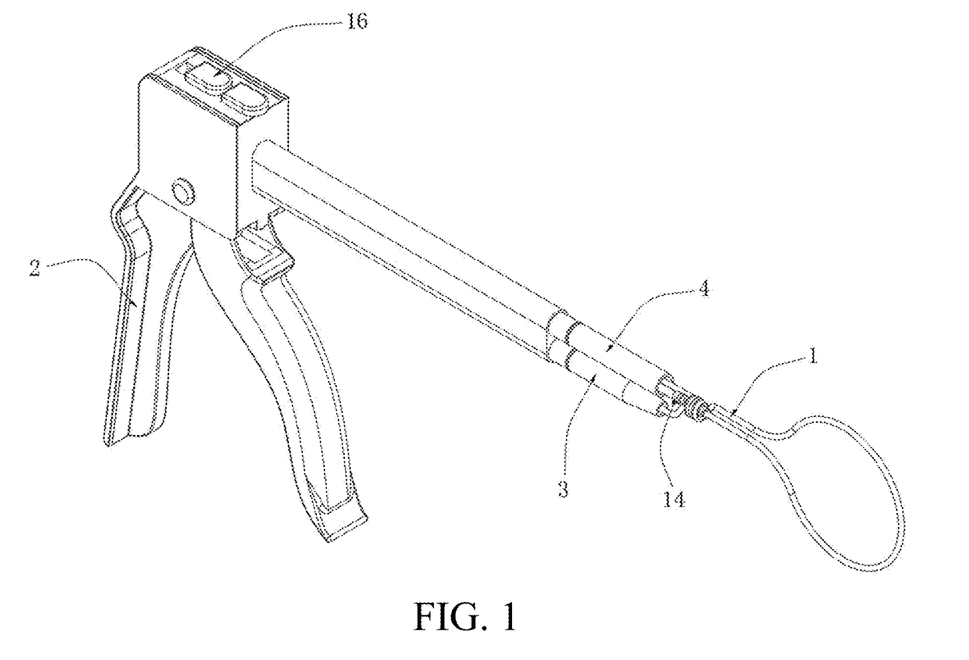
FIG. 1 is a schematic perspective view of the present invention.
Figure 2:
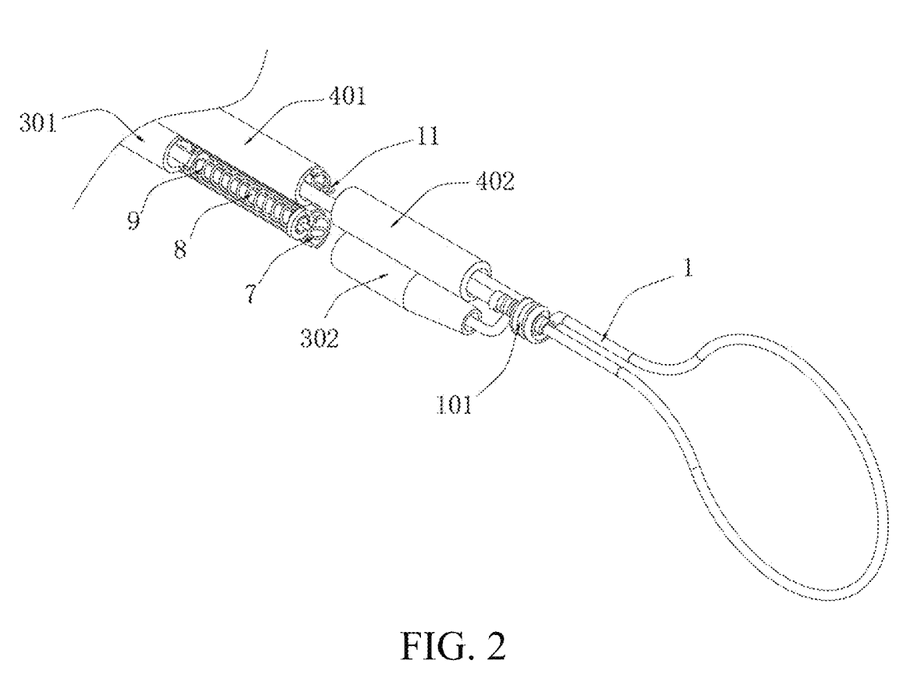
FIG. 2 is an exploded view of a local structure of the present invention.
Figure 3:
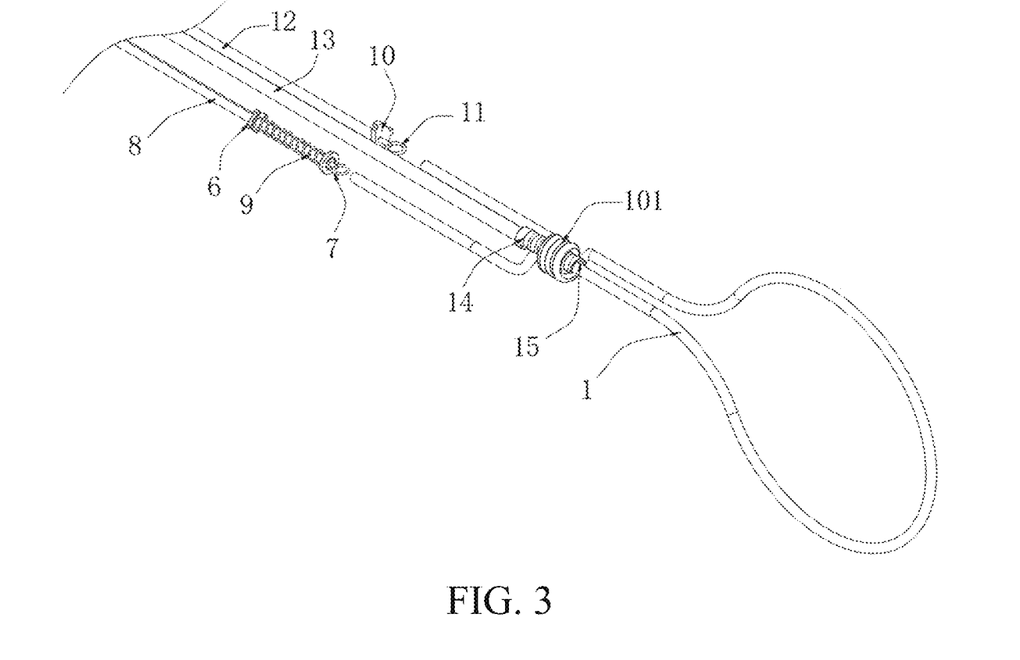
FIG. 3 is an exploded view of a local structure of the present invention.
Figure 4:
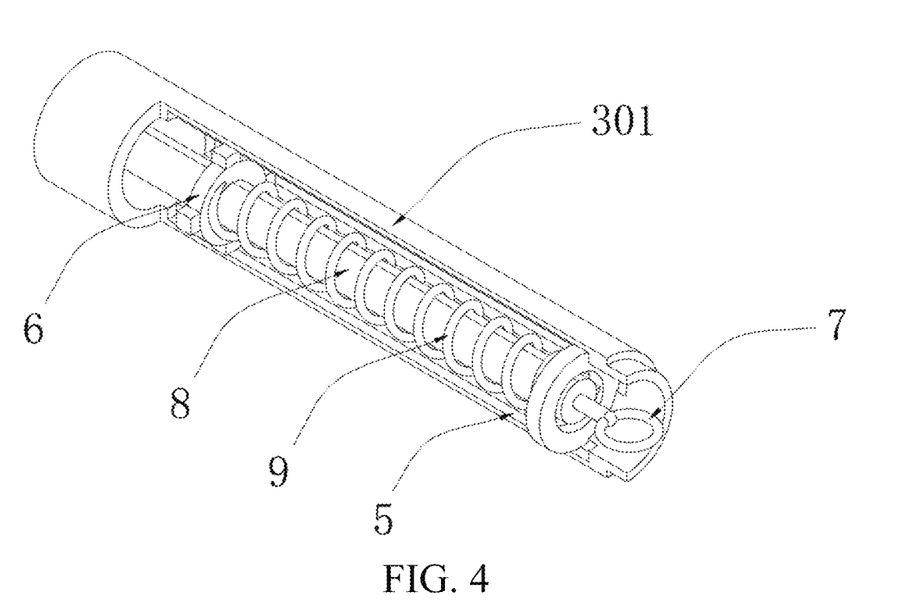
FIG. 4 is a cross-sectional view of a straight pipe portion of the present invention.
Figure 5:
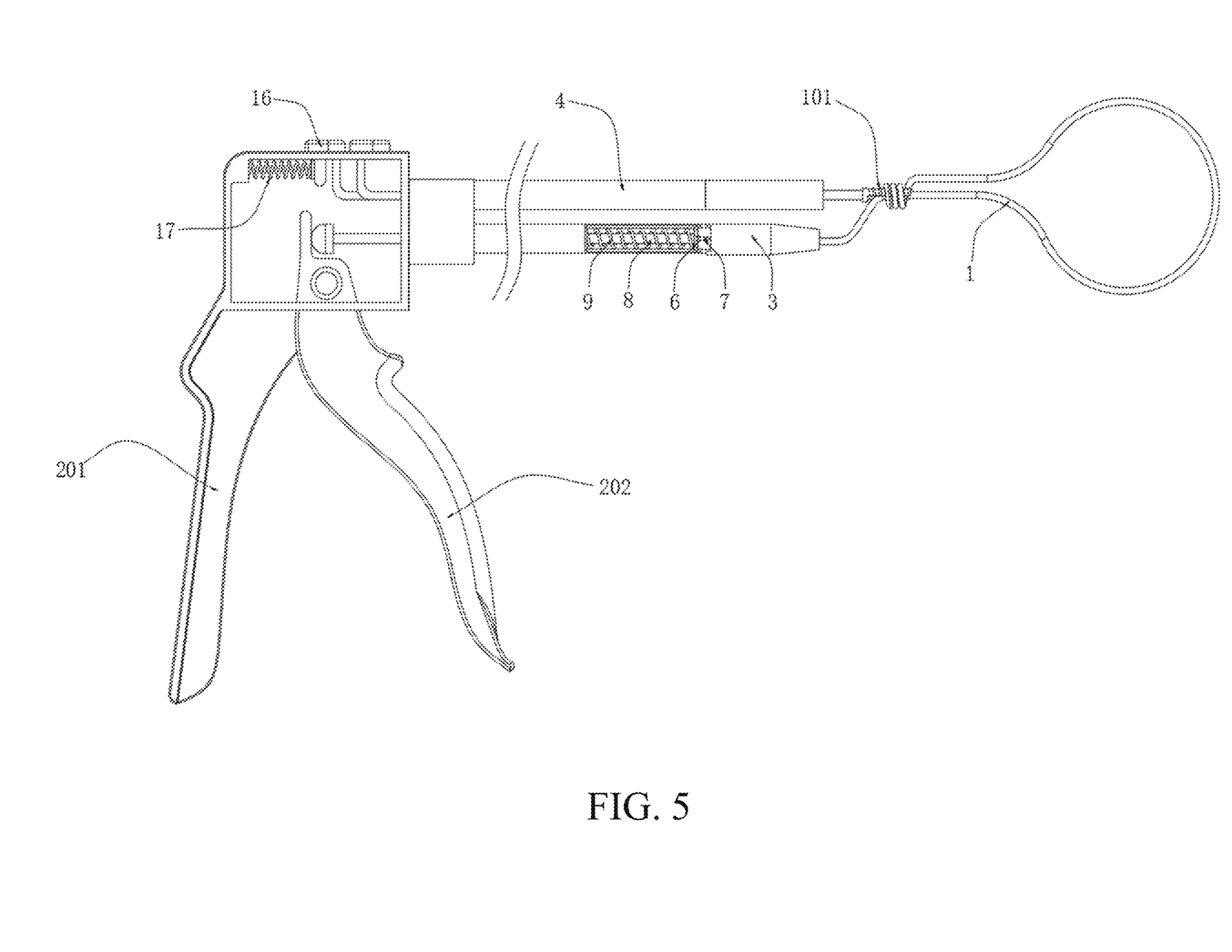
FIG. 5 is a cross-sectional view of the present invention.

Referring to FIG. 1 to FIG. 5, the present invention provides a technical solution: a left atrial appendage ligator comprises a ligature 1 and an operating handle 2, one end of the operating handle 2 is fixedly connected with a support rod, the inner wall of the support rod is fixedly connected with a feeding pipe 3 and a locking pipe 4, a first sliding groove 5 is formed in the inner side wall of the feeding pipe 3, the inner side wall of the first sliding groove 5 is slidably connected with a first sliding block 6, the middle part of the first sliding block 6 is fixedly connected with a feeding push rod 8, one end of the feeding push rod 8 is fixedly connected with a first hook 7, one side of the first sliding block 6 is fixedly connected with a return spring 9, a second sliding groove is formed in the inner side wall of the locking pipe 4, the second sliding groove is internally slidably connected with a second sliding block 10, one end of the second sliding block 10 is fixedly connected with a second hook 11, the other end of the second sliding block 11 is fixedly connected with a locking push rod 12, a sliding cavity is formed in the inner wall, adjacent to the second sliding groove, of the locking pipe 4, a supporting component is inserted in the sliding cavity, one end of the ligature 1 is wound at the middle part of the ligature 1 to form a hanger knot 101 so as to form a loop at the middle part of the ligature 1 in a surrounding manner, and the loop is arranged at one end of the outer wall of the supporting component.

The operating handle 2 comprises a fixed handle 201, the inner side wall of the fixed handle 201 is rotatably connected with a grip 202 through a rotating shaft, the top part of the grip 202 is provided with a push plate matched with the feeding push rod 8, and the other end of the feeding push rod 8 pushes tightly against the side wall of the push plate so as to facilitate pushing of the feeding push rod 8 by the push plate to adjust the size of the loop formed by the ligature 1.

In addition, the other end of the support rod 13 and one end of the locking push rod 12 are each fixedly connected with a push button 16, a horizontal sliding groove matched with the push buttons 16 is formed in the upper surface of the fixed handle 201, and the push buttons 16 are in slip connection with the inner wall of the horizontal sliding groove so as to facilitate controlling of the locking of the ligature and the separation of the sleeve pipe portion from the ligature through the push buttons. The top part of the inner wall of the fixed handle 201 is fixedly connected with a buffer spring 17, and one end of the buffer spring 17 is fixedly connected with one of the push buttons 16. Therefore, after the locking, the buffer spring 17 pushes the push button and then discharge the hanger knot 101, thereby facilitating the operator to cut the ligature.

Finally, the supporting component comprises a supporting rod 13 inserted in the movable cavity, one end of the supporting rod 13 is fixedly connected with a sleeve pipe portion 14, a guide hole 15 for threading the ligature 1 is formed in the middle part of the sleeve pipe portion 14, and a temporary storage groove matched with the ligature is formed in the outer wall of the sleeve pipe portion 14. The temporary storage groove can improve the friction force and avoid automatic falling and locking of the ligature 1.

A method of using the left atrial appendage ligator comprises the following specific steps:

step 1, prearranging the ligature 1 on the sleeve pipe portion to form the hanger knot 101;

step 2, pressing the grip 202 by an operator, extending the ligature 1 out in a surrounding manner to form a ligature ring, and expanding the ligature ring to pass through the outer contour of the left atrial appendage, wherein the size of the ligature ring is set to be 50-70 mm;

step 3, lowering the ligature ring to pass through the outer contour of the left atrial appendage with the aid of a surgical instrument by the operator to a ligation position;

step 4, confirming that when the ligature ring sleeves the ligation position, sliding backwards the push button at the other end of the support rod 13 by the operator to drive the recovery of the sleeve pipe portion 14 so as to separate the ligature 1 from the sleeve pipe portion 14, and simultaneously sliding backwards the push button 16 at one end of the locking push rod 12 to drive the locking of the hanger knot 101 so as to realize automatic knotting; and step 5, cutting off the ligature 1 at the tail part of the hanger knot 101 and taking out the left atrial appendage ligator.

During specific use, the operator presses the handle to compress the grip 202, pushes the feeding push rod 8 through the grip 202 to further push the first sliding block 6 to compress the return spring 9, such that the feeding push rod 8 extends to drive a movable end of the ligature 1 to extend out and the ligature 1 slides in the sleeve pipe portion 14 when extending out. The hanger knot 101 is supported by the sleeve pipe portion 14 so as to effectively avoid the automatic locking of the hanger knot 101. Besides, the temporary storage groove is formed in the surface of the sleeve pipe portion 14, thereby improving the friction force of the surface of the sleeve pipe portion 14 and improving the storage capacity of the ligature 1. After the ligature ring surrounded by the ligature 1 is expanded, the left atrial appendage can be conveniently and quickly sleeved by the operator. Besides, the ligature 1 is automatically contracted by the return spring 9. When the hanger knot 101 needs to be locked, the push button at the other end of the support rod 13 slides backward to drive the recovery of the sleeve pipe portion 14 so as to separate the ligature 1 from the sleeve pipe portion 14, and simultaneously the push button 16 at one end of the locking push rod 12 slides backwards to drive the locking of the hanger knot 101 so as to realize automatic knotting. The ligature 1 is prearranged on the sleeve pipe portion to form the hanger knot 101 so as to avoid knotting during the operation process. During the operation, the knotting can be completed only by locking the hanger knot 101, thereby reducing the operation time and improving the operation efficiency.

Example 2

Referring to FIGS. 2, 3, 4 and 5, in order to achieve the purposes of reducing cost by repeated use and facilitating assembly, the feeding pipe and the locking pipe are arranged in a detachable structure, specifically:

the feeding pipe 3 comprises a straight pipe portion 301 and a guide portion 302, and one end of the guide portion 302 is in threaded connection with the straight pipe portion 301 so as to facilitate the operator to detach the feeding pipe 3 and fix the ligature 1. The locking pipe 4 comprises a fixing portion 401 and a detaching portion 402, and one end of the detaching portion 402 is in threaded connection with the fixing portion 401 so as to facilitate detaching of the locking pipe 4 and fix the other end of the ligature 1.

One end of the ligature 1 threading through the guide portion 302 is attached to the surface of the first hook 7, and the other end of the ligature 1 threading through the detaching portion 402 is attached to the surface of the second hook 11 so as to facilitate change of different ligatures during use each time.

Specifically, during use, when the operator change the ligature, the guide portion 302 and the straight pipe portion 301 are detached in a threaded mode, simultaneously the detaching portion 402 and the fixing portion 401 are detached in a threaded mode, the ligature 1 is wound, knotted and fixed with the first hook 7, the middle part of the ligature 1 is wound to form the hanger knot 101 and hanged on the sleeve pipe portion 14, and the other end of the ligature 1 is threaded through the hanger knot 101, and knotted and fixed with the second hook 11.

The above description is only a preferred embodiment of the present invention, but the protection scope of the present invention is not limited thereto. Any equivalent substitution or change made by a person skilled in the art within the technical scope of the present invention according to the technical solutions of the present invention and the inventive concepts thereof should be covered by the protection scope of the present invention. In the description of the present description, the terms "connect", "install", "fix", "arrange" and the like are understood broadly, for example, the "connect" may be fixed connection or indirect connection through intermediate components without affecting the relationship and technical effects of the components, and may also be an integral connection or a partial connection. As in this case, a person skilled in the art may understand the specific meanings of the terms in the present invention or inventions according to the specific situations.

What is claimed is:

1. A left atrial appendage ligator, comprising a ligature and an operating handle, one end of the operating handle is fixedly connected with a support rod, an inner wall of the support rod is fixedly connected with a feeding pipe and a locking pipe, a first sliding groove is formed in an inner side wall of the feeding pipe, an inner side wall of the first sliding groove is slidably connected with a first sliding block, a middle part of the first sliding block is fixedly connected with a feeding push rod, one end of the feeding push rod is fixedly connected with a first hook, one side of the first sliding block is fixedly connected with a return spring, a second sliding groove is formed in an inner side wall of the locking pipe, the second sliding groove is internally slidably connected with a second sliding block, one end of the second sliding block is fixedly connected with a second hook, the other end of the second sliding block is fixedly connected with a locking push rod, a sliding cavity is formed in the inner sidewall of the locking pipe, adjacent to the second sliding groove, of the locking pipe, a supporting component is inserted in the sliding cavity, one end of the ligature is wound at a middle part of the ligature to form a hanger knot so as to form a loop at the middle part of the ligature in a surrounding manner, and the loop is arranged at one end of an outer wall of the supporting component; the feeding pipe comprises a straight pipe portion and a guide portion, one end of the guide portion is in threaded connection with the straight pipe portion, the locking pipe comprises a fixing portion and a detaching portion; and one end of the detaching portion is in threaded connection with the fixing portion, and the one end of the ligature threading through the guide portion is attached to a surface of the first hook, and the other end of the ligature threading through the detaching portion is attached to a surface of the second hook.

2. The left atrial appendage ligator according to claim 1, wherein the supporting component comprises the support rod inserted in the sliding cavity, one end of the support rod is fixedly connected with a sleeve pipe portion, a guide hole for threading the ligature is formed in a middle part of the sleeve pipe portion, and a temporary storage groove matched with the ligature is formed in an outer wall of the sleeve pipe portion.

3. The left atrial appendage ligator according to claim 2, wherein the operating handle comprises a fixed handle, an inner side wall of the fixed handle is rotatably connected with a grip through a rotating shaft, a top part of the grip is provided with a push plate matched with the feeding push rod, and the other end of the feeding push rod pushes tightly against a side wall of the push plate.

4. The left atrial appendage ligator according to claim 3, wherein the other end of the support rod and one end of the locking push rod are each fixedly connected with a push button, a horizontal sliding groove matched with the push buttons is formed in an upper surface of the fixed handle, and the push buttons are in slip connection with an inner wall of the horizontal sliding groove.

5. The left atrial appendage ligator according to claim 4, wherein a top part of the inner side wall of the fixed handle is fixedly connected with a buffer spring, and one end of the buffer spring is fixedly connected with one of the push buttons.

* * * * *